United States Patent [19]

Larkin

[11] 4,439,193
[45] Mar. 27, 1984

[54] APPARATUS FOR CONNECTING MEDICAL LIQUID CONTAINERS

[75] Inventor: Mark E. Larkin, Lindenhurst, Ill.

[73] Assignee: Abbott Laboratories, North Chicago, Ill.

[21] Appl. No.: 350,468

[22] Filed: Feb. 19, 1982

[51] Int. Cl.³ .............................................. A61M 5/00
[52] U.S. Cl. ...................................... 604/411; 604/29;
604/244; 604/407; 604/905; 141/330
[58] Field of Search ................. 604/93, 174, 177, 178,
604/407, 414, 905, 29, 411, 244; 285/24, 27;
141/329–330, 369, 370, 372, 375

[56] References Cited

U.S. PATENT DOCUMENTS

| | | | |
|---|---|---|---|
| 3,610,241 | 10/1971 | LeMarie | 604/407 |
| 3,833,030 | 9/1974 | Waldbauer, Jr. et al. | 141/375 X |
| 3,853,158 | 12/1974 | Whitty | 141/375 X |
| 4,201,406 | 5/1980 | Dennehey et al. | 285/27 X |
| 4,219,055 | 8/1980 | Wright | 604/407 X |
| 4,296,949 | 10/1981 | Muetterties et al. | 604/174 X |
| 4,333,505 | 6/1982 | Jones et al. | 604/905 X |
| 4,340,052 | 7/1982 | Dennehey et al. | 604/905 X |
| 4,354,490 | 10/1982 | Rogers | 604/905 X |

Primary Examiner—C. Fred Rosenbaum
Assistant Examiner—Michelle N. Lester
Attorney, Agent, or Firm—Robert S. Beiser; Alan R. Thiele

[57] ABSTRACT

An improved apparatus for aseptically connecting medical liquid containers to a length of flexible tubing comprises a port on the container, a pierceable diaphragm within the port, and a hollow tubular piercing pin connected to the length of flexible tubing adapted for penetrating the pierceable diaphragm. An alignment tray having a bag port cavity integrally formed therein is adapted for receiving and fixedly positioning the bag port and the bag. A guide mechanism integrally formed along the length of the tray is constructed to align the piercing pin and allow it to be slidably joined to the bag port without touch contamination of the port or the pin.

23 Claims, 14 Drawing Figures

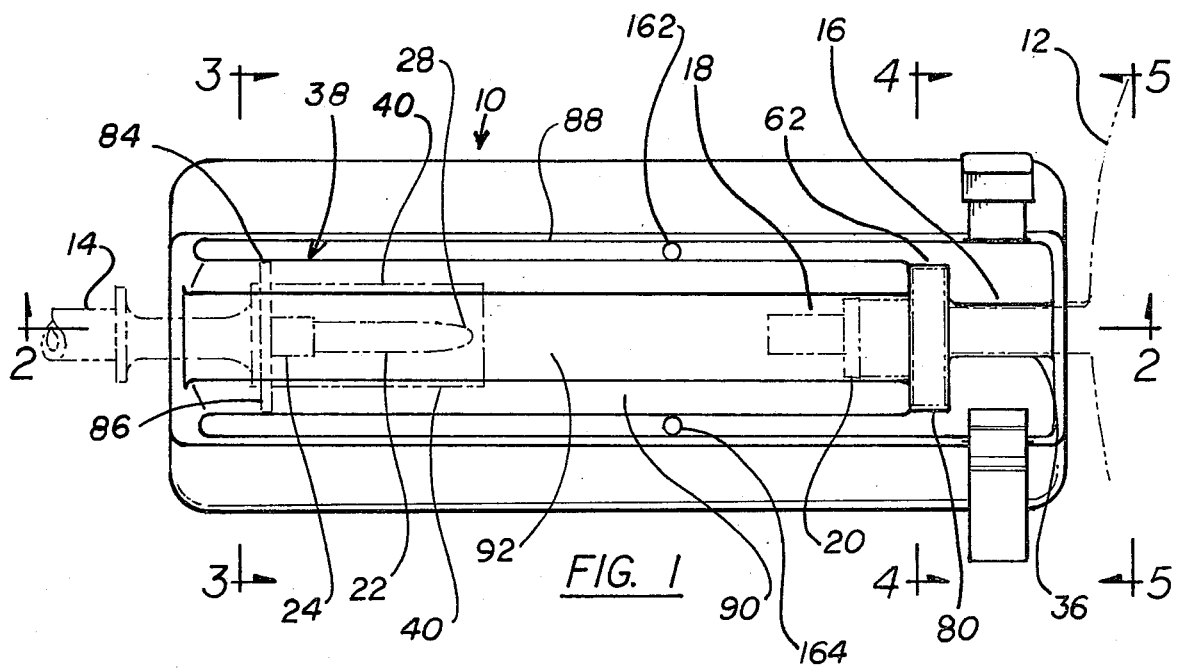
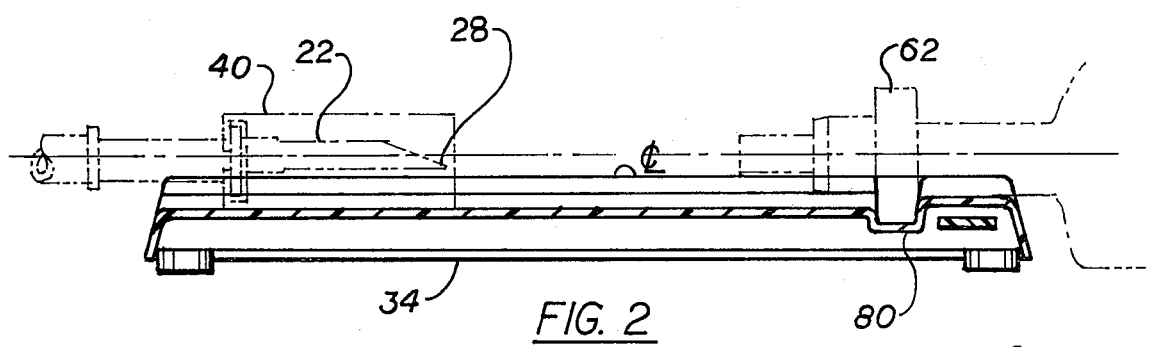
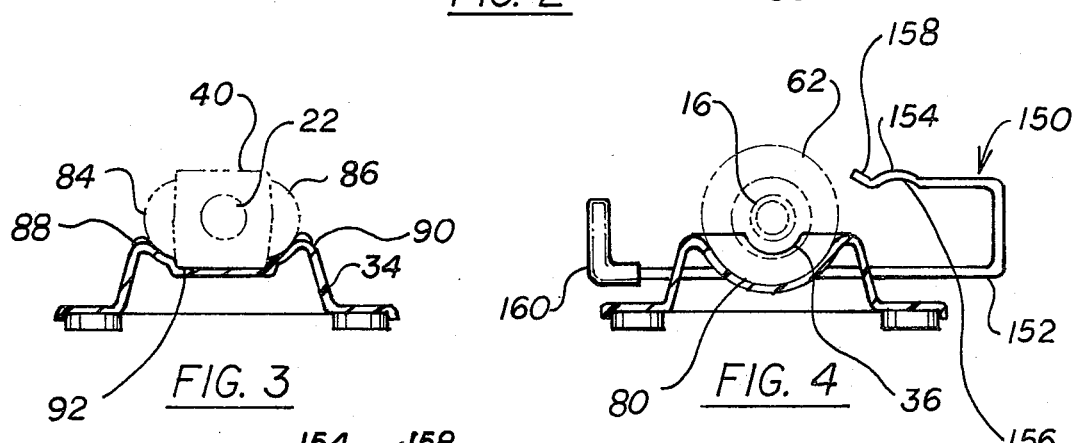
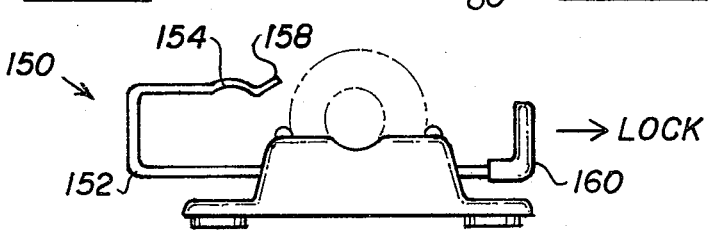

APPARATUS FOR CONNECTING MEDICAL LIQUID CONTAINERS

BACKGROUND OF THE INVENTION

The present invention relates generally to the field of connecting mechanisms for fixedly joining together a length of tubing to a medical liquid container. The connector of the present mechanism was developed specifically for use in continuous ambulatory peritoneal dialysis. The present application is distinguished by the use of an alignment tray which facilitates connection of flexible plastic containers of peritoneal dialysis solution to flexible tubing extending from the peritoneal catheter of the patient.

Prior to the present invention, connectors of various kinds have been used to effectuate rapid and effective junctions between pieces of medical tubing. A requirement of such connectors is that a fluid-tight seal be obtained. Another requirement is that the connection be strongly resistent to inadvertent disengagement, but should be readily disengagable when desired by simple and rapid manual manipulation.

The use of piercing pins adapted for connection to medical liquid containers is commonly known in the art. However, such piercing pins are commonly inserted into a length of flexible tubing extending from the containers in a press-fit connection which is difficult to disengage while in use. At the same time, maintaining the connection in an aseptic condition is essential.

An additional problem in performing aseptic connections in continuous ambulatory peritoneal dialysis is in treating patients who are aged, partially sighted or blind, and have poor manual dexterity. Present connection techniques are difficult or impossible for these individuals to perform. Various attempts to overcome this problem have been developed, as seen in the following U.S. patents:

U.S. Pat. Nos. 4,201,406; 4,030,494; 3,876,234; 4,256,106; Design Patent D-229,518 and an article from the proceedings of an International Symposium in Paris, 1979 entitled "Continuous Ambulatory Peritoneal Dialysis with a Bacterialogical Filter on the Dialysate Infusion Line."

SUMMARY OF THE INVENTION

The foregoing advantages are accomplished and the shortcomings of the prior art are overcome by the improved apparatus for aseptically connecting medical liquid containers to a length of flexible tubing, as seen in the present invention, which comprises a tubular port extending from the container, a pierceable diaphragm positioned within and sealing the port, and a hollow tubular piercing pin connected at its proximal end to the length of flexible tubing. Ordinarily, the flexible tubing is connected to peritoneal catheter and the medical liquid in the container is peritoneal dialysate.

The present invention represents an improvement over the prior art in the use of an alignment tray having a bag port cavity integrally formed therein and adapted for reception and fixed positioning of the bag port and the bag. A guide mechanism integrally formed in the tray is constructed and arranged for slidably aligning the hollow tubular piercing pin with the bag port. As a result, the piercing pin may be joined to the bag port without touch contamination of the bag port or the pin. In addition, the guide means insures that even persons of poor eyesight or poor manual dexterity can easily insert the pin into the port in an aseptic manner.

In a preferred embodiment, a clasp member is enclosed about the piercing pin and is adapted for retaining the piercing pin within the tubular port after they have been joined. The clasp member also prevents touch contamination of the piercing pin and the port. The clasp member usually includes first and second substantially C-shaped body portions hingedly connected to each other, and latching means at opposing ends whch hold the clasp closed about the piercing pin. A tubular shroud distally extends from the clasp member and is constructed for telescopic connection to the tubular port member. Threading is integrally formed about the tubular shroud. A lock nut is concentrically disposed about the tubular port. The lock nut is constructed for threaded engagement with the threading on the tubular shroud. As a result, when the clasp member, with the piercing pin contained therein, is telescopically connected to the tubular port, the lock nut may be rotated so as to fixedly attach the tubular port, piercing pin and clasp member together.

In a preferred embodiment, the alignment tray is adapted for use with the clasp member and lock nut mechanism. A lock nut cavity is integrally formed in the alignment tray and provides clearance from the lock nut when the tubular port is positioned within the bag port cavity. As a result, the lock nut may be rotated within the lock nut cavity so as to engage the threading on the tubular shroud, thereby causing the piercing pin to penetrate the diaphragm and the tubular port to be fixedly attached to the piercing pin.

The piercing pin is usually constructed with a pair of rectangular flanges extending laterally therefrom. The guide mechanism preferably comprises a pair of coaxial ridges or guides integrally formed in and linearly arrayed along the alignment tray. The ridges are constructed for reception of the lateral flange members, and facilitate axial movement of the piercing pin along the alignment tray.

The clasp member preferably has an exterior configuration which is constructed and arranged so as to substantially conform to the width and depth of the guide mechanism. As a result, the clasp member may be received in and linearily advanced along the guide mechanism in substantial axial alignment with said tubular port member until telescopically connected to the port member, or retracted therefrom.

In a preferred emodiment, the guide mechanism comprises both the previously mentioned ridges for guiding the lateral flange members of the hollow tubular piercing pin and a linear trough integrally formed along the base of the alignment tray. The trough is constructed to conform to the width and depth of the clasp member so as to allow linear advancement of the clasp member, with the pin contained therein, along the tray until the piercing pin and clasp member are telescopically connected to the tubular port.

In a preferred embodiment, the clasp member includes one or more absorbent sponges contained therein which are impregnated with an antiseptic solution. The sponges are disposed within each of the substantially C-shaped portions and are constructed and arranged for asepticizing the connection between the tubular port and the piercing pin.

The previously mentioned lock nut, which is used to connect the clasp mechanism to the bag port, has several advantages over the prior art connecting devices. They are:

1 Acts as large, comfortable grip for holding port and removing pin while pin is inserted;
2. Mechanically seats pin in port;
3. Mechanically retains port to pin;
4. Prevents the clasp from disengaging from the pin, even if both latches are accidentally disengaged.

BRIEF DESCRIPTION OF THE DRAWINGS

FIG. 1 of the drawings is a top view of an improved apparatus for connecting medical liquid containers to a length of flexible tubing.

FIG. 2 of the drawings is a vertical section of the connecting apparatus of FIG. 1.

FIG. 3 of the drawings is a vertical section taken along axis 3—3 of the connecting apparatus of FIG. 1.

FIG. 4 of the drawings is a vertical section of the connecting apparatus of FIG. 1 taken along axis 4—4.

FIG. 5 of the drawings is an end view of the connecting apparatus of FIG. 1.

DETAILED DESCRIPTION OF THE PREFERRED EMBODIMENT

Figure 6:
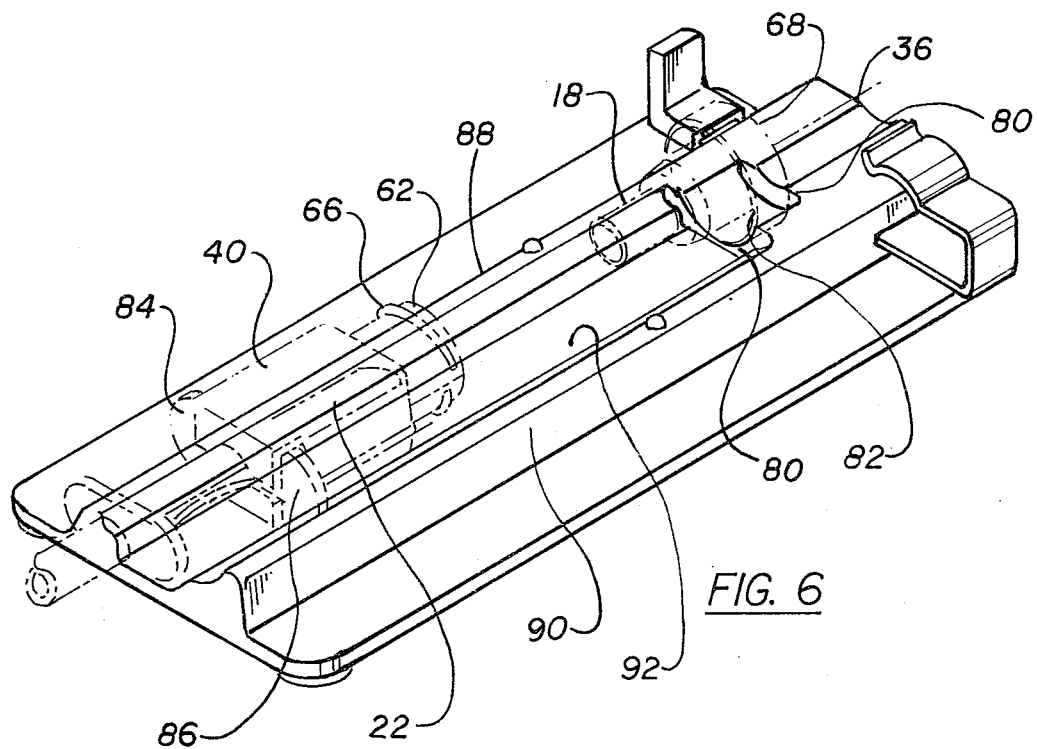
FIG. 6 of the drawings is a front perspective view of the connecting apparatus of FIG. 1.

While this invention is susceptible of embodiment in many different forms, there is shown in the drawings and will herein be described in detail several specific embodiments, with the understanding that the present disclosure is to be considered as an exemplification of the principles of the invention and is not intended to limit the invention to the embodiments illustrated.

As best seen in FIGS. 1 and 2 of the drawings, apparatus 10 is constructed for aseptically connecting medical liquid container 12 (shown in phantom lines) to a length of flexible tubing 14 (shown in phantom lines). A tubular port member 16 extends from container 12. Extending from tubular port 16 is a rigid tubular insert 18 having a radial flange 20 concentrically disposed thereabout, adapted for limiting the insertion of rigid insert 18 into port 16. In order to provide access to liquid in container 12, a piercing pin 22 is provided. A length of flexible tubing 14 extends from piercing pin 22 and is adapted for the conveyance of liquid. Piercing pin 22 is inserted into rigid insert 18 and hence, into tubular port 16 so as to be retained therein, thereby allowing the passage of liquid from container 12 to flexible tubing 14.

Figure 7:
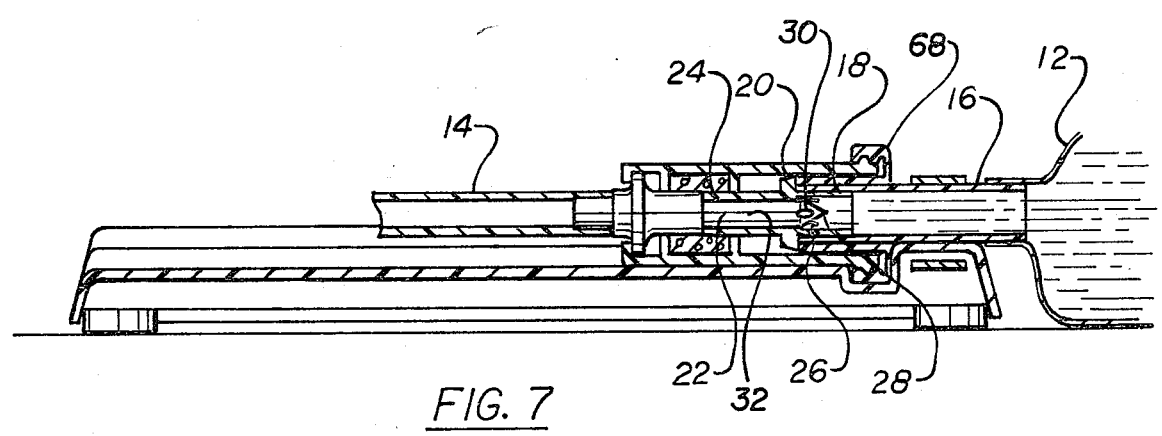
FIG. 7 of the drawings is a vertical section of the connecting apparatus of FIGS. 1–6 showing in particular a tubular piercing pin slidably affixed to the tubular port of a medical liquid container.
Figure 8:
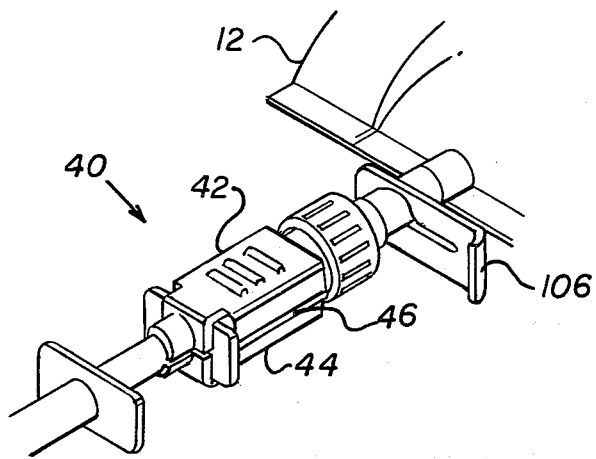
FIG. 8 of the drawings is a front perspective view of the connection between a medical liquid container and a length of flexible plastic tubing utilizing the clasp of FIG. 7.

As best seen in FIG. 7 of the drawings, disposed within tubular insert 18 is a pierceable diaphgram 26 which is penetrated by sharpened tip 28 of piercing pin 22 upon insertion into tubular port 16. Following such insertion, medical liquid contained within container 12 may pass from container 12, through tubular port 16, piercing pin 22, and out flexible tubing 14. In order to allow the flow of liquid through piercing pin 22, sharpened tip 28 has an open orifice 30 proximate thereto and opening into lumen 32 which extends through piercing pin 22.

Best seen in FIG. 2 is alignment tray 34 having a bag port cavity 36 integrally formed therein. Bag port cavity 36 is adapted for reception and fixed positioning of bag port 16 therein. Alignment tray 34 also has guide mechanism 38 integrally formed therein along a substantial portion of the length of tray 34. Guide mechanism 38 is constructed to align hollow tubular piercing pin 22 and allow it to be slid in a linear manner along tray 34 until telescopically received by and joined to rigid insert 18 and thereby bag port 16, all without touch contamination of bag port 16 or piercing pin 22.

In this regard, in a preferred embodiment, piercing pin 22 is enclosed within a clasp member 40, best seen in FIGS. 8 through 12 of the drawings. Clasp member 40 comprises first C-shaped portion 42 and second C-shaped portion 44, hingedly connected along mid-line 46. Clasp member 40 includes latching mechanism 48 at opposing ends 50 and 52. Clasp member 40 is constructed and arranged for pivotal enclosure of piercing pin 22 and for the fixed positioning of piercing pin 22 relative to tubular port 16.

Figure 10:
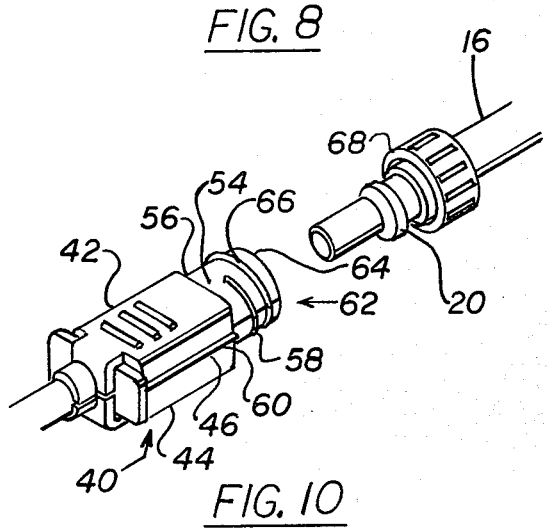
FIG. 10 of the drawings is a front perspective view of the connecting device of FIG. 8 showing the tubular port removed from the piercing pin and clasp member.
Figure 11:
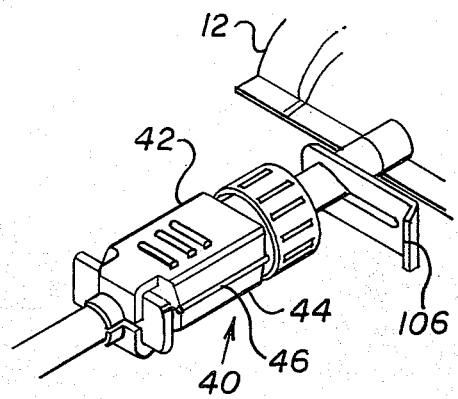
FIG. 11 of the drawings is a front perspective view of the connecting device of FIGS. 8 through 10 showing in particular a new bag and port assembly being threadably connected to a piercing pin and a new clasp member.

As best seen in FIG. 10 of the drawings, clasp member 40 includes a first semicircular flange 54 extending for the distal end 56 of first substantially C-shaped body portion 42. A second semicircular flange 58 is of substantially the same size as first semicircular flange 54 and extends concentrically from distal end 60 of second substantially C-shaped body portion 44. First semicircular flange 54 and second semicircular flange 58 are positioned and constructed of the same size so as to meet upon closure of clasp member 40, thereby forming a tubular end port 62 extending from the distal end 64 of clasp member 40. Threading 66 extends helically around and is integrally formed on first semicircular flange 54 and second semicircular flange 58 so as to form a helical array about tubular end port 62. A mating locknut 68 is positioned concentrically around tubular port 16 which extends from medical liquid container 12. Locknut 68 is constructed and arranged for threaded engagement with the threading 66 on tubular end port 62. In addition, locknut 68 is constructed, when rotated on end port 16, to come into abutment against circular flange 20. As a result, by mean of clasp member 40, tubular port 16 and tubular piercing pin 22 may be fixedly connected.

Figure 12:
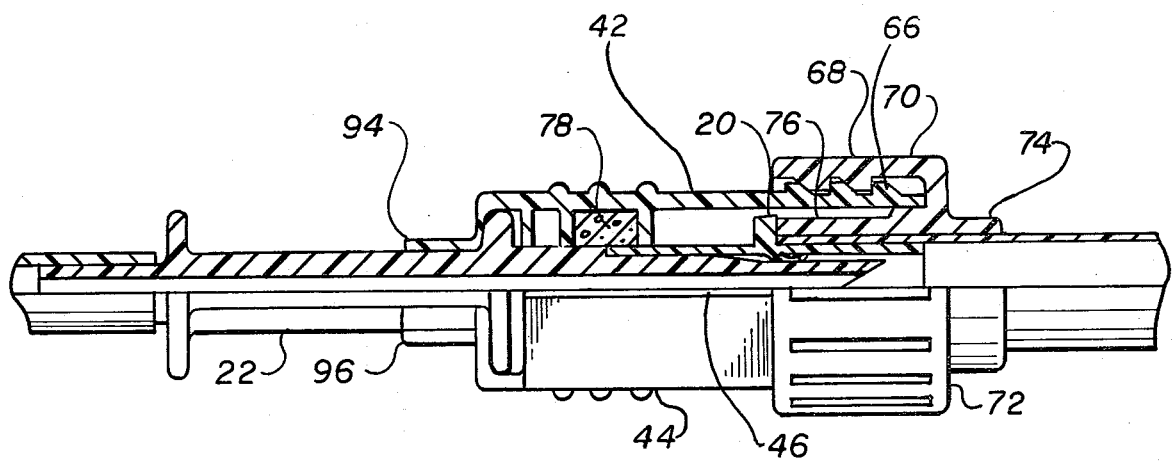
FIG. 12 of the drawings is a side view, partially broken away, of the clasp member of FIGS. 8 through 11.

As best seen in FIG. 12, in one embodiment, locknut 68 is formed as a cap having side wall 70 and end wall 72. A circular orifice 74 is formed in the center of locknut 68 which is of the proper size for telescopic reception of tubular port 16. Locknut 68 also includes inner rim 76 which is merely a tubular extension of orifice 74 into locknut 68. Rim 76 is adapted for abutment against radial flange 20. Thus, as locknut 68 is threadably connected onto threading 66, further rotation is prevented by abutment against flange 20. At this point, tubular port 16 and piercing pin 22 are fixedly attached.

Figure 9:
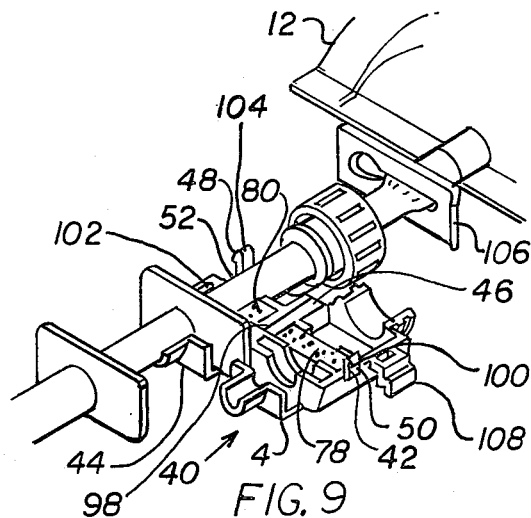
FIG. 9 of the drawings is a front perspective view of the connecting device of FIG. 8 showing in particular the clasp member in an open position.

As best seen in FIGS. 9 and 12 of the drawings, clasp member 40 preferably includes absorbent sponges 78 and 80 which contain an antiseptic solution suc as povidone iodine. Absorbent sponges 78 and 80 are positioned within clasp member 40 for encirclement and enclosure of the connection between piercing pin 22 and tubular port 16.

Returning to FIGS. 1 through 3 of the drawings, alignment tray 34 is designed for slidably aligning clasp member 40 to tubular bag port 16 and rigid insert 18. Clasp member 40 encloses tubular piercing pin 22 so that advancement of clasp member 40 along alignment try 34 permits slidably joining bag port 16 to tubular piercing pin 22.

FIG. 6 of the drawings also shows threading 66 about clasp member 40 is integrally formed and helically arrayed about tubular shroud 62 extending from clasp member 40. As stated previously, locknut 68 is concentrally disposed about tubular port 16 and is constructed and arranged for threaded engagement with threading 66 on tubular shroud 62. As a result, tubular port 16 may be fixedly attached to clasp member 40 and thereby to tubular piercing pin 22.

To allow this attachment, locknut cavity 80 is integrally formed in alignment tray 34. Locknut cavity 80 is constructed and arranged for clearance from locknut 68 so that when tubular port 16 is positioned within bag port cavity 36, locknut 68 may be rotated within locknut cavity 80. This causes engagement of threading 66 on tubular shroud 62 to threading 82 within locknut 68 (FIG. 7). As a result, piercing pin 22 is advanced into and through diaphragm 26 and tubular port 16 is fixedly attached to piercing pin 22.

As further seen in FIGS. 1 and 6 of the drawings, in one embodiment, hollow tubular piercing pin 22 includes a pair of flange members 84 and 86 which extend laterally from piercing pin 22 for fitment with guide mechanism 38. Guide mechanism 38 comprises a pair of coaxial ridges 88 and 90 which are linearly arrayed along alignment tray 34. Ridges 88 and 90 are of sufficient height, are spaced apart far enough and are shaped to conform to the exterior of lateral flange members 84 and 86. As a result, when piercing pin 22 is placed within guide mechanism 38, raised ridges 88 and 90 guide the axial movement of piercing pin 22 along alignment tray 34.

As best seen in FIG. 6 of the drawings, an additional part of guide mechanism 38 is a trough 92 integrally formed in the base of alignment tray 34 between raised ridges 88 and 90. Trough 92 is of the proper width and depth to receive clasp member 40. Trough 92 extends the length of alignment tray 34 so as to guide clasp member 40 with hollow tubular piercing pin 22 contained therein along tray 34. As a result, attachment of clasp member 40 to locknut 68 and connection between piercing pin 22 and tubular port 16 is facilitated; i.e., little manual dexterity and visual control is required.

As best seen in FIG. 3, lateral flanges 84 and 86 extend to both sides of clasp member 40. However, flanges 84 or 86 may be a radial flange which extends circumferentially around hollow tubular piercing pin 22. In that instance, trough 92 would be substantially semicircular in shape so as to receive radial flange 84 and clasp member 40.

As best seen in FIG. 12, substantially C-shaped portions 42 and 44 include semicircular slots 94 and 96 oppositely disposed on and adapted for reception of piercing pin 22. As a result, clasp member 40 with antiseptic sponges 78 and 80 may be tightly enclosed about piercing pin 22 so as to prevent leakage.

As further seen in FIG. 9, clasp member 40 preferably comprises a modular unit constructed of an injection molded plastic such as polypropylene, or other commonly known medical plastics and having integrally formed hinge 98 along mid-line 36 between first portion 42 and second portion 44. Male latch member 100 extends from C-shaped portion 42 and female slot member 102 extends radially from C-shaped portion 44. When first C-shaped portion 42 is pivotally rotated relative to second C-shaped portion 44, male latch 100 engages female slot 102 so as to lock in a closed position until release is desired. Second male member 104 is positioned on and extends fom second C-shaped portion 44 and is adapted for mating with second female member 106. As a result, clasp member 30 may be opened, using a one handed operation. Converging digital pressure on first tab 108 and second tab 110 (not shown) causes latch mechanism 48 to disengage, thereby opening clasp 40.

As mentioned previously, the present apparatus is designed primarily for use in connecting a peritoneal catheter (not shown) to a flexible container of peritoneal dialysis solution 12 when performing continuous ambulatory peritoneal dialysis. In order to accomplish this, flexible tubing 14 extends from the peritoneal dialysis cathether.

OPERATION OF THE SYSTEM

As seen in FIG. 1, piercing pin 22 is enclosed within clasp member 40. Piercing pin 22 and tubular port 14 are then placed onto alignment tray 34. Tubular port 16 is placed into bag port cavity 36 and locknut 68 is placed into locknut cavity 80. Piercing pin 22 with radial flanges 84 and 86 extending therefrom is placed between raised ridges 88 and 90. At the same time, clasp member 40, which is enclosed about piercing pin 22 is received by linear trough 92. Clasp member 40 and piercing pin 22 are then linearly advanced along the axis of alignment tray 34 until piercing pin 22 is telescopically received by rigid tubular insert 18. Piercing pin 22 is advanced by means of rotating locknut 68 so as to threadedly engage threading 66, (FIG. 10) thereby advancing piercing pin 22 until tubular insert 18 abuts against raised shoulder 24. Piercing pin 22 is thereby further advanced so as to penetrate diaphragm 26 thereby exposing orifice 30 to peritoneal dialysis solution contained within container 12 and port 16. Solution thereby passes through orifice 30 and lumen 32, through piercing pin 22, through flexible tubing 14, through a peritoneal catheter and into the peritoneum of the patient.

Once peritoneal dialysis solution is drained into the peritoneum, of the patient, clasp member 40 is withdrawn from alignment tray 34 with piercing pin 22 and bag port 16 thereby also being removed. Flexible liquid container 12 is then rolled up and carried by the patient in a position proximate the peritoneal catheter.

In peritoneal dialysis the peritoneal solution ordinarily remains in the patient's peritoneum for a period of approximately four hours. Following the four-hour-period, the flexible liquid container 12 is reopened and lowered below the level of the peritoneal catheter. Clasp member 40 with piercing pin 22 and tubular port 16 is then placed back onto alignment tray 34 and slide clamp 160 closed. Locknut 68 is then rotated in a counterclockwise direction so as to release clasp member 40. A new container 12 is then placed adjacent to alignment tray 34 with the tubular port 16 and locknut 68 placed in respective cavities 80 and 36. The procedure is then repeated.

Figure 13:
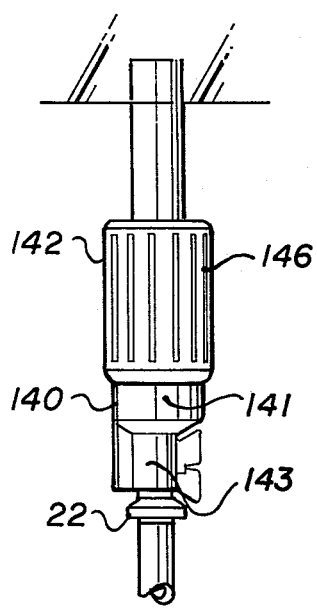
FIG. 13 of the drawings is a side view of an alternative embodiment of a connecting device for medical liquid containers.
Figure 14:
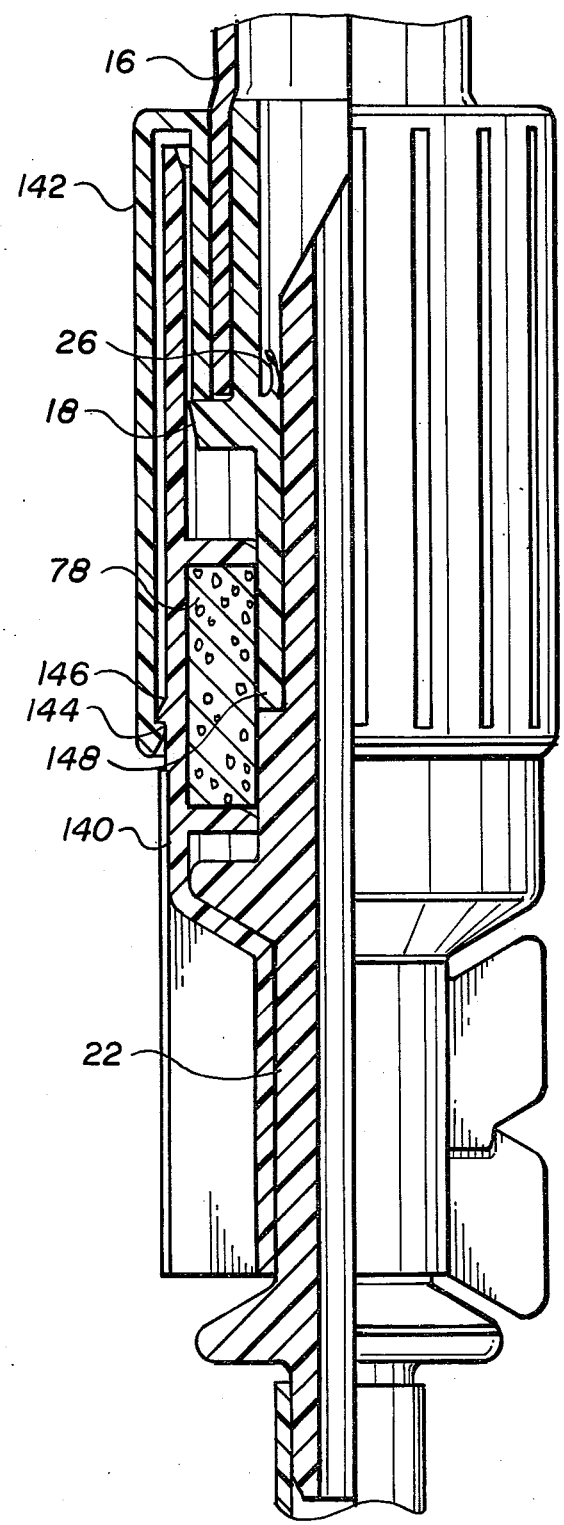
FIG. 14 of the drawings is a side view, partially in section, of the connecting device of FIG. 13.

As best seen in FIGS. 13 and 14 of the drawings, in an alternative embodiment, piercing pin 22 and tubular port 16 may be enclosed within an alternative embodiment of clasp 40, numbered clasp 140. Clasp 140 includes first C-shaped portion 141 and second C-shaped portion 143 but does not contain external threading such as threading 66. Similarly, extending from tubular port 16 is a port shroud 142 which contains a snap lock 144. When piercing pin 22 penetrates diaphragm 26, port shroud 142 telescopically receives clasp member 140. Port shroud 142 includes includes inwardly directed bevel or snap lock 144 which is adapted for snapping engagement against outwardly directed bevel 146 which extends from clasp member 140. As a result, when piercing pin 22 and tubular port 16 are fully engaged, clasp member 140 is fully extended into port shroud 142 so that inwardly directed bevel 44 snaps over outwardly directed bevel 146, thereby fastening port 16 to piercing pin 22. Port shroud 142 is sufficiently flexible, however, to allow port 16 and port shroud 142 to be snapped off of clasp member 140. Alternatively, port shroud 142 may be threadably attached to clasp member 140. The cylindrical shape of port shroud 142 and clasp member 140 allows the clasp member 140 to be rotated, giving a wiping action of sponge 178 against pin/port interface 148.

An additional feature of the invention may be seen in FIGS. 4 and 5 of the drawings. A slidable lock mechanism 150 is movably attached to alignment tray 34 for selectively fixing tubular bag port tubular bag port 16 within bag port cavity 36. Slidable lock mechanism 150 comprises a manually displaceable slide member 152 cross axially disposed through alignment tray 34. Slide member 152 has a gripping member 154 attached thereto which extends from the end of slide member 152 and upward and rearwardly therefrom. Gripping member 154 includes a semicircular portion 156 adapted for engagement with bag port 16 and a raised end portion 158 which is slanted upward so as to facilitate sliding up and over bag port 16. Slide member 152 is sufficiently flexible to allow gripping member 154 to be snapped over bag port 16, but is sufficiently stiff to retain bag port 16 when engaged thereto. A handle 160 is positioned on the proximal end of slide member 152 so as to facilitate pulling of slide member 152 and thereby gripping member 156 onto bag port 16 or pushing slide member 152 thereoff so as to disengage gripping member 154 from port 16.

Further seen in FIG. 1 of the drawings are indicators 162 and 164 which extend vertically from ridges 88 and 90. Indicators 162 and 164 are positioned on ridges 88 and 90 so as to correspond to the proper position for lateral flanges 84 and 86 when piercing pin 22 is fully extended into port 16. Because of the fact that they are raised in a buttonlike configuration, persons having poor visual acuity or manual dexterity are able to digitally ascertain when a connection has been fully completed between piercing pin 22 and tubular port 16.

In a preferred embodiment, clasp members 40 and 140 as well as tubular piercing pin 22, rigid insert 18 and port shroud 142 are constructed of clear or translucent thermoplastic materials such as acrylic. Tubular port 16 and flexible tubing 14 are preferably constructed of flexible polyvinylchloride or other clear, flexible, translucent, thermoplastic materials. Other thermoplastic materials include polypropylene, polyethylene, acrylinitrile, butadiene styrene, and polycarbonate. Piercing pin 22 may also be constructed of other rigid medical grade plastics such as polyethylene terepthalate.

As further seen in FIG. 12, clasp member 40 preferably includes a flat planar surface 70 on its dorsal side. Surface 70 is flat in order to facilitate sliding of clasp member 40 forward or backward on alignment tray 34.

The foregoing description and drawings merely explain and illustrate the invention, and the invention is not limited thereto, except insofar as the appended claims are limited to those skilled in the art who have the disclosure before them and are able to make modifications and variations therein without departing from the scope of the invention.

I claim:
1. An improved apparatus for aseptically connecting medical liquid containers to a length of flexible tubing comprising:
   a tubular port member extending from the medical liquid container;
   a pierceable diaphragm positioned within and sealing said tubular port member;
   a hollow tubular piercing pin connected at its proximal end to said length of flexible tubing and having a sharpened tip at its distal end adapted for penetration of said pierceable diaphragm and further describing a plurality of flange members extending laterally therefrom;
   an alignment tray having a cavity integrally formed therein adapted for the reception and fixed positioning of said tubular port member therein;
   a clasp member constructed and arranged for the selective enclosure of said piercing pin and retention of said piercing pin within said tubular port member, said clasp member including first and second substantially C-shaped portions hingedly connected to each other and further including latching means at opposing ends thereof;
   a tubular shroud distally extending from said clasp member constructed and arranged for telescopic connection to said tubular port member;
   threading means integrally formed and helically arrayed about said tubular shroud;
   lock nut means concentrically disposed about said tubular port member, constructed and arranged for threadable engagement with said threading means on said tubular shroud;
   a linear trough integrally formed along the base of said alignment tray, said trough being constructed and arranged so as to substantially conform to the width and depth of said clasp member; and
   a lock nut cavity integrally formed in said alignment tray, constructed and arranged for clearance from said lock nut when said tubular port member is positioned within said alignment tray;
   whereby said clasp member with said hollow tubular piercing pin contained therein may be snugly received in and linearly advanced along said linear trough in substantial axial alignment with said tu- bular port member so that said piercing pin penetrates said pierceable diaphragm and said threading means on said tubular shroud threadably engages said lock nut so that when said lock nut is rotated within said lock nut cavity, said container will be fixedly attached to said flexible tubing without touch contamination of said port member or said piercing pin.

2. The connecting device as disclosed in claim 1 wherein said clasp member includes a plurality of absorbent sponge members containing an antiseptic solution disposed within each of said substantially C-shaped portions, are constructed and arranged for asepticizing the connection between said tubular port and said piercing pin.

3. The connecting device as described in claim 1 and further comprising a rigid tubular insert member fixedly attached within and sealing said tubular port member, said rigid tubular insert member having a radial flange extending therefrom, adapted for limiting the insertion of said rigid tubular insert member into said tubular port member, with said pierceable diaphragm being integrally formed and positioned within said rigid tubular insert member.

4. The connecting device as disclosed in claim 1 wherein said tubular port member includes a radial flange member disposed about its distal end adapted for engagement with said clasp member.

5. The connecting device as disclosed in claim 1 wherein said hollow tubular piercing pin includes a radial flange member extending therefrom adapted for engagement with said clasp member.

6. The connecting device as disclosed in claim 3 or 4 or 5 wherein said clasp member is constructed and arranged for reception of and engagement with one or more of said radial flanges so as to fixedly position said tubular port relative to said hollow tubular piercing pin.

7. The connecting device as disclosed in claim 1 wherein each of said substantially C-shaped portions defines a plurality of semicircular slots oppositely disposed thereon and adapted for reception and enclosure of said tubular port member and said flexible tubing.

8. The connecting device as disclosed in claim 2 wherein said antiseptic solution comprises povidone iodine.

9. The connecting device as disclosed in claim 1 wherein said clasp member comprises a modular thermoplastic unit having an integrally formed flexible hinge between said first and second portions, integrally formed latch members oppositely disposed on said first and second portions, and integrally formed tabs for facilitating selective digital closure and opening of said connecting device.

10. The apparatus as disclosed in claim 1 and further comprising:
slidable lock means movably attached to said alignment tray for the selective fixation of said tubular bag port within said slidable lock means comprising:
a manually displaceable slide member cross axially disposed through said alignment tray, said slide member having a gripping member attached thereto constructed and arranged for engagement with said tubular bag port when disposed in a first position, and for clearance from said bag port when in a second opposite position, and a handle member oppositely disposed from said gripping member adapted for facilitating manual displacement of said slide member, as required.

11. The apparatus as disclosed in claim 1 and further comprising tactile indicia means for disclosing when said clasp member is fully advanced into engagement with said tubular port member.

12. An improved apparatus for aseptically connecting medical liquid containers to a length of flexible tubing comprising:
a tubular port member extending from the medical liquid container;
a pierceable diaphragm positioned within and sealing said tubular port member;
a hollow tubular piercing pin connected at its proximal end to said length of flexible tubing and having a sharpened tip at its distal end adapted for penetration of said pierceable diaphragm and further describing a plurality of flange members extending laterally therefrom;
an alignment tray having a cavity integrally formed therein adapted for the reception and fixed positioning of said tubular port member therein and further describing coaxial ridge guide means formed along a substantial portion of the length of said alignment tray, said guide means being constructed and arranged for substantial axial alignment of said tubular port member with said piercing pin and slidable reception of said laterally extending flange members;
a clasp member constructed and arranged for the selective enclosure of said piercing pin and retention of said piercing pin within said tubular port member, said clasp member including first and second substantially C-shaped portions hingedly connected to each other and further including latching means at opposing ends thereof;
a tubular shroud distally extending from said clasp member constructed and arranged for telescopic connection to said tubular port member;
threading means integrally formed and helically arrayed about said tubular shroud;
lock nut means concentrically disposed about said tubular port member, constructed and arranged for threadable engagement with said threading means on said tubular shroud;
a linear trough integrally formed along the base of said alignment tray, said trough being constructed and arranged so as to substantially conform to the width and depth of said clasp member; and
a lock nut cavity integrally formed in said alignment tray, constructed and arranged for clearance from said lock nut when said tubular port member is positioned within said alignment tray;
whereby said clasp member with said hollow tubular piercing pin contained therein may be snugly received in and linearly advanced along said guide means and said linear trough in substantial axial alignment with said tubular port member so that said piercing pin penetrates said pierceable diaphragm and said threading means on said tubular shroud threadably engages said lock nut so that when said lock nut is rotated within said lock nut cavity, said container will be fixedly attached to said flexible tubing without touch contamination of said port member or said piercing pin.

13. The connecting device as disclosed in claim 12 wherein said clasp member includes a plurality of absorbent sponge members containing an antiseptic solution disposed within each of said substantially C-shaped portions, are constructed and arranged for asepticizing the connection between said tubular port and said piercing pin.

14. The connecting device as described in claim 12 and further comprising a rigid tubular insert member fixedly attached within and sealing said tubular port member, said rigid tubular insert member having a radial flange extending therefrom, adapted for limiting the insertion of said rigid tubular insert member into said tubular port member, with said pierceable diaphragm being integrally formed and positioned within said rigid tubular insert member.

15. The connecting device as disclosed in claim 12 wherein said tubular port member includes a radial flange member disposed about its distal end adapted for engagement with said clasp member.

16. The connecting device as disclosed in claim 12 wherein said hollow tubular piercing pin includes a radial flange member extending therefrom adapted for engagement with said clasp member.

17. The connecting device as disclosed in claim 14 or 15 or 16 wherein said clasp member is constructed and arranged for reception of and engagement with one or more of said radial flanges so as to fixedly position said tubular port member relative to said hollow tubular piercing pin.

18. The connecting device as disclosed in claim 12 wherein each of said substantially C-shaped portions defines a plurality of semicircular slots oppositely disposed thereon and adapted for reception and enclosure of said tubular port member and said flexible tubing.

19. The connecting device as disclosed in claim 13 wherein said antiseptic solution comprises povidone iodine.

20. The connecting device as disclosed in claim 12 wherein said clasp member comprises a modular thermoplastic unit having an integrally formed flexible hinge between said first and second portions, integrally formed latch members oppositely disposed on said first and second portions, and integrally formed tabs for facilitating selective digital closure and opening of said connecting device.

21. The apparatus as disclosed in claim 12 and further comprising:
slidable lock means movably attached to said alignment tray for the selective fixation of said tubular bag port within said slidable lock means comprising:
a manually displaceable slide member cross axially disposed through said alignment tray, said slide member having a gripping member attached thereto constructed and arranged for engagement with said tubular bag port when disposed in a first position, and for clearance from said bag port when in a second opposite position, and a handle member oppositely disposed from said gripping member adapted for facilitating manual displacement of said slide member, as required.

22. The apparatus as disclosed in claim 12 and further comprising tactile indicia means for disclosing when said clasp member is fully advanced into engagement with said tubular port member.

23. An apparatus for connecting and disconnecting a peritoneal catheter to a flexible container of peritoneal dialysis solution when performing continuous ambulatory peritoneal dialysis comprising:
a tubular port member extending from the medical liquid container;
a pierceable diaphragm positioned within and sealing said tubular port member;
a hollow tubular piercing pin connected at its proximal end to said length of flexible tubing and having a sharpened tip at its distal end adapted for penetration of said pierceable diaphragm and further describing a plurality of flange members extending laterally therefrom;
an alignment tray having a cavity integrally formed therein adapted for the reception and fixed positioning of said tubular port member therein and further describing coaxial ridge guide means formed along a substantial portion of the length of said alignment tray, said guide means being constructed and arranged for substantial axial alignment of said tubular port member with said piercing pin and slidable reception of said laterally extending flange members;
a clasp member constructed and arranged for the selective enclosure of said piercing pin and retention of said piercing pin within said tubular port member, said clasp member including first and second substantially C-shaped portions hingedly connected to each other and further including latching means at opposing ends thereof;
a tubular shroud distally extending from said clasp member constructed and arranged for telescopic connection to said tubular port member;
threading means integrally formed and helically arrayed about said tubular shroud;
lock nut means concentrically disposed about said tubular port member, constructed and arranged for threadable engagement with said threading means on said tubular shroud;
a linear trough integrally formed along the base of said alignment tray, said trough being constructed and arranged so as to substantially conform to the width and depth of said clasp member; and
a lock nut cavity integrally formed in said alignment tray, constructed and arranged for clearance from said lock nut when said tubular port member is positioned within said alignment tray;
whereby said clasp member with said hollow tubular piercing pin contained therein may be snugly received in and linearly advanced along said guide means and said linear trough in substantial axial alignment with said tubular port member so that said piercing pin penetrates said pierceable diaphragm and said threading means on said tubular shroud threadably engages said lock nut so that when said lock nut is rotated within said lock nut cavity, said container will be fixedly attached to said flexible tubing without touch contamination of said port member or said piercing pin.

* * * * *